(12) United States Patent
Martinez et al.

(10) Patent No.: US 6,713,044 B2
(45) Date of Patent: Mar. 30, 2004

(54) SYNTHESIS OF [$^2$H$_1$, $^{13}$C], [$^2$H$_2$, $^{13}$C] AND [$^2$H$_3$, $^{13}$C]METHYL ARYL SULFIDES

(75) Inventors: Rodolfo A. Martinez, Santa Fe, NM (US); Marc A. Alvarez, Santa Fe, NM (US); Louis A. Silks, III, Los Alamos, NM (US); Clifford J. Unkefer, Los Alamos, NM (US)

(73) Assignee: The Regents of the University of California, Los Alamos, NM (US)

( * ) Notice: Subject to any disclaimer, the term of this patent is extended or adjusted under 35 U.S.C. 154(b) by 0 days.

(21) Appl. No.: 10/342,577

(22) Filed: Jan. 14, 2003

(65) Prior Publication Data
US 2003/0153789 A1 Aug. 14, 2003

Related U.S. Application Data

(63) Continuation-in-part of application No. 10/075,046, filed on Feb. 13, 2002, now abandoned.

(51) Int. Cl.$^7$ .................... A61K 51/00; C07C 321/12
(52) U.S. Cl. ................................ 424/1.81; 568/38
(58) Field of Search .............. 424/1.65, 1.81; 568/38, 39, 44

(56) References Cited

PUBLICATIONS

CA:133:163989 abs of Journal of Labelled Compounds and Radiopharmaceutical by Chaudhary et al 43(7) pp. 683–691 2000.*
CA:124:24229 abs of Chem. Res. in Toxicology by Huwe et al 9(1) pp. 215–22 1966.*
CA:101:109832 abs of Helvetica Chim. Acta by Gabriel 67(4) pp. 1070–82 1984.*
Organic Process Research & Development by Martinez et al 6 pp. 851–854 2002.*
CA:129:4391 abs of Magnetic Resonance in Chemistry by Sergeyeva et al 36(4) pp. 255–260 1998.
CA:139:133068 abs of J. Labelled Compounds and Pharmaceuticals by Coumbarides et al 46(4) pp. 291–296 2003.
CA:69:9021 abs of Kozelmenyek by Jancso et al 16 (3) pp. 181–90 1968.

* cited by examiner

Primary Examiner—Jean F. Vollano
(74) Attorney, Agent, or Firm—Bruce H. Cottrell

(57) ABSTRACT

The present invention is directed to labeled compounds, [$^2$H$_1$, $^{13}$C], [$^2$H$_2$, $^{13}$C] and [$^2$H$_3$, $^{13}$C]methyl aryl sulfides wherein the $^{13}$C methyl group attached to the sulfur of the sulfide includes exactly one, two or three deuterium atoms and the aryl group is selected from the group consisting of 1-naphthyl, substituted 1-naphthyl, 2-naphthyl, substituted 2-naphthyl, and phenyl groups with the structure

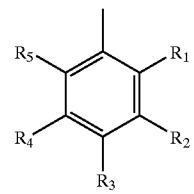

wherein $R_1$, $R_2$, $R_3$, $R_4$, and $R_5$ are each independently, hydrogen, a $C_1$–$C_4$ lower alkyl, a halogen, an amino group from the group consisting of $NH_2$, NHR and NRR' where R and R' are each a $C_1$–$C_4$ lower alkyl, a phenyl, or an alkoxy group. The present invention is also directed to processes of preparing [$^2$H$_1$, $^{13}$C], [$^2$H$_2$,$^{13}$C] and [$^2$H$_3$, $^{13}$C]methyl aryl sulfides wherein the $^{13}$C methyl group attached to the sulfur of the sulfide includes exactly one, two or three deuterium atoms. The present invention is also directed to the labeled compounds of [$^2$H$_1$, $^{13}$C]methyl iodide and [$^2$H$_2$, $^{13}$C] methyl iodide.

14 Claims, No Drawings

SYNTHESIS OF [²H₁, ¹³C], [²H₂, ¹³C] AND [²H₃, ¹³C]METHYL ARYL SULFIDES

RELATED APPLICATIONS

This application is a continuation-in-part of application Ser. No. 10/075,046, filed on Feb. 13, 2002, now abandoned, by Martinez et al.

STATEMENT REGARDING FEDERAL RIGHTS

This invention was made with government support under Contract No. W-7405-ENG-36 awarded by the U.S. Department of Energy. The government has certain rights in the invention.

FIELD OF THE INVENTION

The present invention relates to labeled compounds and more particularly to compounds labeled with carbon-13 and hydrogen-2.

BACKGROUND OF THE INVENTION

Stable isotope labeled amino acids and nucleotides are required for structural and mechanistic studies of proteins and oligonucleotides. In addition, isotopically labeled biologically active compounds are required for many phases of drug discovery and development including elucidation of biosynthetic pathways, pharmacokinetics, and drug metabolism. For many applications, site-specific $^{13}C$ or combined $^{13}C$ and $^2H$ labeling are required. While a number of stable isotope labeled compounds are available from companies such as Sigma-Aldrich Chemicals, a need remains for other labeled synthetic precursors.

Methyl aryl sulfides such as methyl phenyl sulfide have been used in a wide number of reactions to make a large number of such biomolecules and other important synthetic precursors. For example, methyl phenyl sulfide can be used as a nucleophilic synthon and is easily converted into an electrophilic synthon. While methyl phenyl sulfide could provide a chemically stable and non-volatile carrier for the valuable $^{13}C$ and $^2H$ labels, the preparation of few isotopically labeled methyl phenyl sulfides has been previously accomplished. One example of an isotopically labeled methyl phenyl sulfide labeled at the methyl group is shown by Chaudhary et al., J. Labelled Cpd. Radiopharm., 43, 683–691 (2000), although that sulfide wasn't described or suggested as a synthetic reagent for synthesis of labeled compounds. Availability of other significant [²H₁, ¹³C], [²H₂, ¹³C] and [²H₃, ¹³C]methyl phenyl sulfides would allow researchers to take advantage of the wealth of chemistry that has been done using unlabeled methyl phenyl sulfide.

As carbon-13 is separated from its lighter isotope by cyrogenic distillation of carbon monoxide (CO), all labeled carbons are derived ultimately from CO. The highly efficient conversion of CO to useful chemical precursors is perhaps the most unique aspect of stable isotope labeling technology. Any inefficiencies in the early synthetic steps add greatly to the overall expense of isotope labeling. Thus, considerable efforts have been directed to the development of methods for the preparation of useful synthetic precursors or synthons. This effort has given rise to efficient large-scale methods for the synthesis of methane, methanol, methyl iodide, sodium formate, potassium cyanide and carbon dioxide. These methods are the foundation of all labeling chemistry. The most useful of the electrophilic one-carbon precursors, methyl iodide and carbon dioxide, are difficult to store and use efficiently due to their high volatility.

As spectroscopic instrumentation and techniques continue to improve, there is a drive to study ever more complicated bio-systems. This has lead to demands for more complex labeling patterns in biomolecules. In the past, the simple introduction of a labeled atom site-specifically without stereospecificity was the major thrust for stable isotope labeling and the first generation of labeled synthons served this effort well. Increasingly, in today's labeling climate, in addition to site-specific labeling, the requirement for stereospecificity has been added. This includes both the ability to stereospecific label chiral compounds as well as the ability to differentiate between prochiral centers with deuterium or carbon. Additional synthons as starting materials will address those growing demands.

It is an object of the present invention to provide labeled compounds.

SUMMARY OF THE INVENTION

In accordance with the purposes of the present invention, as embodied and broadly described herein, the present invention provides labeled compounds, [²H₁, ¹³C], [²H₂, ¹³C] and [²H₃, ¹³C]methyl aryl sulfides wherein the $^{13}C$ methyl group attached to the sulfur of the sulfide includes exactly one, two or three deuterium atoms and the aryl group is selected from the group consisting of 1-naphthyl, substituted 1-naphthyl, 2-naphthyl, substituted 2-naphthyl, and phenyl groups with the structure

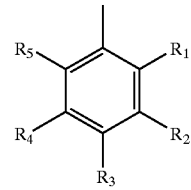

wherein $R_1$, $R_2$, $R_3$, $R_4$ and $R_5$ are each independently, hydrogen, a $C_1$–$C_4$ lower alkyl, a halogen, an amino group from the group consisting of $NH_2$, NHR and NRR' where R and R' are each a $C_1$–$C_4$ lower alkyl, a phenyl, or an alkoxy group.

The present invention further provides a process of preparing a [²H₁, ¹³C], [²H₂, ¹³C] and [²H₃, ¹³C]methyl aryl sulfide wherein the $^{13}C$ methyl group attached to the sulfur of the sulfide includes exactly one, two or three deuterium atoms and the aryl group is selected from the group consisting of 1-naphthyl, substituted 1-naphthyl, 2-naphthyl, substituted 2-naphthyl, and phenyl groups with the structure

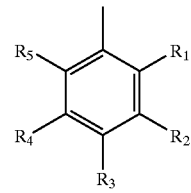

wherein $R_1$, $R_2$, $R_3$, $R_4$ and $R_5$ are each independently, hydrogen, a $C_1$–$C_4$ lower alkyl, a halogen, an amino group from the group consisting of $NH_2$, NHR and NRR' where R and R' are each a $C_1$–$C_4$ lower alkyl, a phenyl, or an alkoxy group, the process including reacting [¹³C]methanol with hydriodic acid to form a product mixture including volatile

[$^{13}$C]methyl iodide, passing said volatile [$^{13}$C]methyl iodide directly into a biphasic mixture including aqueous sodium hydroxide, benzene, and an arylthiol having the structure

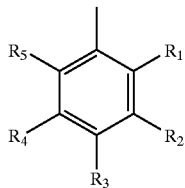

wherein $R_1$, $R_2$, $R_3$, $R_4$ and $R_5$ are each independently a $C_1$–$C_4$ lower alkyl, a halogen, an amino group from the group consisting of $NH_2$, NHR or NRR' where R and R' are each a $C_1$–$C_4$ lower alkyl, a phenyl or an alkoxy group and maintaining said biphasic mixture for time sufficient to form the, [$^2H_1$, $^{13}$C], [$^2H_2$, $^{13}$C] and [$^2H_3$, $^{13}$C]methyl aryl sulfide

DETAILED DESCRIPTION

Methyl aryl sulfides are useful organic reagents that allows for the construction of many useful biochemicals and materials. Isotopically labeled methyl aryl sulfide can be used to introduce a carbon-13 [$^{13}$C] and a hydrogen-2 or deuterium label [$^2H$] into such biochemicals and materials.

As used herein, the term "aryl" means a monovalent monocyclic or bicyclic aromatic hydrocarbon radical of 6 to 10 ring atoms, and optionally substituted independently with one, two, three, four or five substituents selected from alkyl, haloalkyl, cycloalkyl, halo, nitro, cyano, —OR (where R is hydrogen, alkyl, haloalkyl, cycloalkyl, optionally substituted phenyl), acyl, and —COOR (where R is hydrogen or alkyl). More specifically, the term "aryl" includes, but is not limited to 1-naphthyl, substituted 1-naphthyl, 2-naphthyl, substituted 2-naphthyl, and phenyl groups with the structure

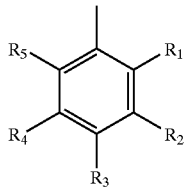

wherein $R_1$, $R_2$, $R_3$, $R_4$ and $R_5$ are each independently a lower alkyl, i.e., a $C_1$–$C_4$ alkyl such as methyl, ethyl, n-propyl, iso-propyl, butyl, isobutyl, and tert-butyl, a halogen such as chloro, bromo or iodo, an amino group such as $NH_2$, NHR or NRR' where R and R' are each a lower alkyl or aryl as described above, or an alkoxy group such as O-alkyl or O-aryl where the alkyl is a lower alkyl as described above or an aryl as described above.

As used herein, the term "[$^2H_1$, $^{13}$C]" means exactly one deuterium atom, the term "[$^2H_2$,$^{13}$C]" means exactly two deuterium atoms, and the term "[$^2H_3$, $^{13}$C]" means exactly three deuterium atoms within the respective compound.

[$^2H_1$, $^{13}$C], [$^2H_2$,$^{13}$C] and [$^2H_3$,$^{13}$C]Methyl aryl sulfides can be made from [$^2H_1$, $^{13}$C], [$^2H_2$, $^{13}$C] and [$^2H_3$, $^{13}$C] methyl alcohol in a one step process as shown below. The [$^2H_1$,$^{13}$C], [$^2H_2$, $^{13}$C] and [$^2H_3$,$^{13}$C]methyl aryl sulfides can be used as a non-volatile carrier of the desired labels, i.e., carbon and hydrogen labels. Methyl aryl sulfides without the isotopic substitution can be made in high yields by the same process.

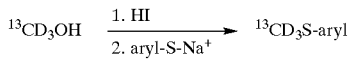

Availability of the [$^2H_1$, $^{13}$C], [$^2H_2$, $^{13}$C] and [$^2H_3$, $^{13}$C]methyl aryl sulfides having the structure

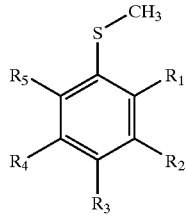

wherein $R_1$, $R_2$, $R_3$, $R_4$ and $R_5$ are each independently a lower alkyl, i.e., a $C_1$–$C_4$ alkyl such as methyl, ethyl, n-propyl, iso-propyl, butyl, isobutyl, and tert-butyl, a halogen such as chloro, bromo or iodo, an amino group such as $NH_2$, NHR or NRR' where R and R' are each a lower alkyl or aryl as described above, or an alkoxy group such as O-alkyl or O-aryl where the alkyl is a lower alkyl as described above or an aryl as described above, and the methyl group attached to the sulfide includes exactly one, two or three deuterium atoms will allow researchers to take advantage of the wealth of chemistry that has been done using unlabeled methyl phenyl sulfide.

The present invention provides [$^2H_1$, $^{13}$C], [$^2H_2$, $^{13}$C] and [$^2H_3$, $^{13}$C]methyl aryl sulfides, i.e., [$^{13}$C]methyl aryl sulfide wherein the methyl group includes exactly one, two or three deuterium atoms. For those molecules with exactly one or two deuterium atoms, such isotopically differentiated methyl groups can be attractive for a variety of applications. For example, a chirally differentiated isopropyl group, i.e., —CH($^{13}$CDH$_2$)($^{13}$CD$_2$H) can be produced.

The present invention provides efficient large scale one-pot processes for the preparation of methyl phenyl sulfides, e.g., [$^2H_1$,$^{13}$C], [$^2H_2$, $^{13}$C] and [$^2H_3$, $^{13}$C]methyl phenyl sulfides from [$^2H_1$, $^{13}$C], [$^2H_2$, $^{13}$C] and [$^2H_3$, $^{13}$C]methanol. Such processes can avoid the inevitable losses resulting from the isolation of labeled methyl iodide. Such methyl aryl sulfides provide a chemically stable and non-volatile carrier for the valuable $^{13}$C and $^2H$ labels.

In addition, [$^{13}$C]methyl iodide including exactly one or two deuterons has been prepared from [$^2H_1$, $^{13}$C] and [$^2H_2$, $^{13}$C]methyl aryl sulfides including exactly one or two deuterons. Such materials, i.e., [$^2H_1$, $^{13}$C] and [$^2H_2$, $^{13}$C]methyl iodides have not previously been available.

[$^{13}$C]Methanol is commercially available. Thus, labeled methyl iodide could be derived from the readily available labeled methanol by refluxing the methanol in hydriodic acid (47–57% by weight in water) and collecting the volatile components. The resultant material can then be dried by treatment with a molecular sieve and re-distilled to yield [$^{13}$C]methyl iodide in yields varying from 62% to 94% according to prior publications. Unfortunately, this easy synthesis suffers a drawback and potential hazard from the fact that methyl iodide is both volatile and carcinogenic. To avoid these problems, the process of the present invention combines two synthetic steps into a single pot process and avoids the isolation of [$^{13}$C]methyl iodide.

In the process of the present invention, [$^{13}$C]methyl aryl sulfides can be prepared in a high yield (>95%) process by refluxing [$^{13}$C]methanol in hydriodic acid (47% by weight in water) to produce volatile methyl iodide, and passing the volatile methyl iodide into a biphasic mixture of thiophenol, sodium hydroxide, water and benzene for time sufficient to form [$^{13}$C]methyl phenyl sulfide.

The [$^{13}$C, $^{2}$H$_1$]methyl iodide and [$^{13}$C, $^{2}$H$_2$]methyl iodide can be prepared from [$^{13}$C, $^{2}$H$_1$]methyl phenyl sulfide and [$^{13}$C, $^{2}$H$_2$]methyl phenyl sulfide. Initially, quantitative deprotonation of either [$^{13}$C]methyl phenyl sulfide or [$^{13}$C, $^{2}$H$_3$]methyl phenyl sulfide can be accomplished by reaction with sec-butyllithium at $-78°$ C. Use of sec-butyllithium is preferred over n-butyllithium because the need for co-solvents and other additives can be eliminated. Based on NMR analysis, the deuterium content of the product sulfides was equivalent to the deuterated starting materials. Finally, the labeled methyl iodides are formed in good yield by slowly heating benzyl iodide and the respective methyl phenyl sulfide to around 160° C. and collecting the volatile methyl iodide products using a liquid nitrogen cooled trap.

The present invention is more particularly described in the following examples which are intended as illustrative only, since numerous modifications and variations will be apparent to those skilled in the art.

EXAMPLE 1

[$^{13}$C]Methyl phenyl sulfide was prepared as follows. A one-liter, two-neck flask was fitted with an argon inlet adapter and an air-cooled condenser. This flask was charged with 46.2 gram (g) (1.40 mole) [$^{13}$C]methanol (99% $^{13}$C) and 726 milliliter (ml) (4.20 mole, 3.00 equivalents (eq)) hydroiodic acid (HI) (47% by weight solution in water). The air-cooled condenser was fitted with an outlet adapter, which in turn was attached (via a short piece of Tygon® tubing) to a long solvent trap immersed in an ice-water bath. This ice-cooled solvent trap was connected to an inlet adapter on a two-liter, two-neck flask containing a vigorously stirring biphasic mixture of 169.7 g (1.54 mole, 1.10 eq) thiophenol and 140 g (3.50 mole, 2.50 eq) of sodium hydroxide (NaOH) in a mixture of 400 ml benzene and 300 ml water. The second neck of this flask was fitted with an isopropanol/dry ice-cooled condenser with an argon outlet. The [$^{13}$C] methanol/HI solution was then heated at 85° C. for 2 hours, and then heating was discontinued. Again, any [$^{13}$C]methyl iodide, which had collected in the ice-cooled trap was transferred to the sodium-thiophenoxide mixture, and this mixture was allowed to stir overnight. The mixture was then transferred to a separatory funnel containing 400 ml of ethyl ether (Et$_2$O), the organic phase was washed with three 100 ml portions of water, and then dried over sodium sulfate (Na$_2$SO$_4$). Removal of the solvents under reduced pressure gave 168 g (95.6% theoretical yield) of [$^{13}$C]methyl phenyl sulfide as a clear, colorless oil: $^1$H NMR (500 MHz, CDCl$_3$) $\partial$2.33–2.61 (d, 3H, J=139.6 Hz), 7.11–7.26(m, 5H); $^{13}$C NMR (125 MHz, CDCl$_3$) $\partial$138.4, 128.8, 126.7, 125.0, 15.9.

EXAMPLE 2

[$^{2}$H$_3$, $^{13}$C]Methyl phenyl sulfide was prepared as follows from [$^{2}$H$_4$, $^{13}$C]methanol using the procedure of Example 1. From 36.6 g (0.987 mole) of [$^{2}$H$_4$, $^{13}$C]methyl alcohol, 540 ml (2.96 mole, 3.00 e q) HI (47% aqueous solution), 120 g (1.09 mole, 1.10 eq) thiophenol, and 98.7 g (2.47 mole, 2.50 eq) NaOH was obtained 125 g (98.6% theoretical yield) [$^{2}$H$_3$, $^{13}$C]-methyl phenyl sulfide as a clear, slightly yellow oil: $^1$H NMR (300 MHz, CDCl$_3$) $\partial$7.10–7.26 (m, 5H); $^{13}$C(75 MHz, CDCl$_3$) $\partial$138.4, 128.8, 126.7, 125.0, {16.0, 15.7, 15.4, 15.1, 14.9, 14.6, 14.3 (septet, J=21.3 Hz)}.

EXAMPLE 3

[$^{2}$H$_1$, $^{13}$C]Methyl phenyl sulfide was prepared as follows. A 250 ml round bottom flask fitted with a magnetic stir bar was charged with 5.00 g (39.9 mmole) of [$^{13}$C]methyl phenyl sulfide. About 70 ml of tetrahydrofuran (THF) were added, and the stirred solution was cooled to $-78°$ C. in a dry ice bath. 1.3 M sec-butyl lithium (sec-BuLi) (32.3 ml, 41.9 millimoles (mmole), 1.05 eq) was added via syringe, and the solution was stirred at $-78°$ C. for 1.5 hours. After this time, the reaction was quenched with 10 ml of $^2$H$_2$O. The mixture was poured into a separatory funnel containing enough water to dissolve the insoluble material, and the aqueous phase was extracted with two 50 ml portions of methylene chloride (CH$_2$Cl$_2$). The combined organic layers were dried over Na$_2$SO$_4$, and the product (4.98 g, 99% theoretical yield) was obtained through careful removal of the solvents under reduced pressure: $^1$H NMR (500 MHz, CDCl$_3$) $^{13}$C NMR (125 MHz, CDCl$_3$) $\partial$2.33–2.61 (d, 2H, J=139 Hz), 7.13–7.35 (m, 5H); $^{13}$C NMR (125 MHz, CDCl$_3$) $\partial$138.3, 128.8, 126.6, 125.0, [15.77, 15.61, 15.43(t, J=21.5 Hz)}.

EXAMPLE 4

[$^{2}$H$_2$, $^{13}$C]Methyl phenyl sulfide was prepared as follows. Using the procedure of Example 3, [$^{2}$H$_2$, $^{13}$C]methyl phenyl sulfide was prepared from [$^{2}$H$_3$, $^{13}$C]methyl phenyl sulfide. From 10.0 g of [$^{2}$H$_3$, $^{13}$C]methyl phenyl sulfide (78.0 mmole) and 72 ml of 1.3 M n-BuLi (93.6 mmole, 12 eq) stirring at $-78°$ C. for 3 hours was obtained, after a H$_2$O quench, 9.83 g (99%) of product as a clear, pale-yellow oil; $^1$H NMR (500 MHz, CDCl$_3$) $\partial$2.30–2.58(d, 1H, J=139 Hz), 7.12–7.29(m, 5H); $^{13}$C NMR (125 MHz, CDCl$_3$) $^{13}$C NMR (125 MHz, CDCl$_3$) $\partial$138.4, 128.8, 126.6, 125.0, [15.70, 15.53, 15.35, 15.18, 15.01 (pentet, J=21.3 Hz)}.

EXAMPLE 5

[$^{2}$H$_1$, $^{13}$C]Methyl iodide was prepared as follows. A two-neck 100 ml round bottom flask was fitted with an air inlet adapter and a short path condenser. 12.0 g (95.1 mmole) of [$^{2}$H$_1$, $^{13}$C]methyl phenyl sulfide was added to the flask, along with 41.5 g (0.190 mole, 2.00 eq) of benzyl iodide. The reaction flask was heated gradually to 110° C. under a steady stream of argon. The reaction darkened as [$^{2}$H$_1$, $^{13}$C]methyl iodide passed from the reaction flask into a dry ice/isopropanol cooled receiving flask. Heating was continued for 7 hours and the collected product purified by cryogenic distillation to give 11.4 g (83% theoretical yield) of a clear, colorless liquid: $^1$H NMR (500 MHz, CDCl$_3$) $\partial$2.01–2.31 (d, 2H, J=151 Hz);) $^{13}$C NMR (125 MHz, CDCl$_3$) $\partial${$-23.3$, $-23.5$, $-23.7$ (t, J=23.0 Hz)}.

EXAMPLE 6

[$^{2}$H$_2$, $^{13}$C]Methyl iodide was prepared as follows. An alternate procedure was used to obtain [$^{13}$C, $^{2}$H$_2$]methyl iodide. 10.0 g (78.6 mmole) of [$^{2}$H$_2$, $^{13}$C]methyl phenyl sulfide and 34.3 g (0.157 mole, 2.00 eq) of benzyl iodide were heated between 80–90° C. under a vacuum over a seven hour period. [$^{2}$H$_2$, $^{13}$C]Methyl iodide was collected in a liquid nitrogen (N$_2$) cooled flask, and purified by cryogenic distillation over 4 Å molecular sieves to yield 9.07 g (79.6% theoretical yield) of product as a clear, colorless liquid: $^1$H NMR (500 MHz, CDCl$_3$) $\partial$1.99–2.(d, 1H, J=151 Hz); $^{13}$C NMR (125 MHz, CDCl$_3$) $\partial${23.2, $-3.4$, $-23.5$, $-23.7$, $-23.9$ (pentet, J=23.2 Hz)}.

Although the present invention has been described with reference to specific details, it is not intended that such details should be regarded as limitations upon the scope of the invention, except as and to the extent that they are included in the accompanying claims.

What is claimed is:

1. A labeled compound from the group of [$^2$H$_1$, $^{13}$C], [$^2$H$_2$, $^{13}$C] and [$^2$H$_3$, $^{13}$C]methyl aryl sulfides wherein the $^{13}$C methyl group attached to the sulfur of the sulfide includes exactly one, two or three deuterium atoms and the aryl group is selected from the group consisting of 1-naphthyl, substituted 1-naphthyl, 2-naphthyl, substituted 2-naphthyl, and phenyl groups with the structure

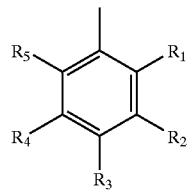

wherein $R_1$, $R_2$, $R_3$, $R_4$ and $R_5$ are each independently, hydrogen, a $C_1$–$C_4$ lower alkyl, a halogen, an amino group from the group consisting of NH$_2$, NHR and NRR' where R and R' are each a $C_1$–$C_4$ lower alkyl, a phenyl, or an alkoxy group.

2. The compound of claim 1 wherein said aryl is selected from the group consisting of phenyl groups with the structure

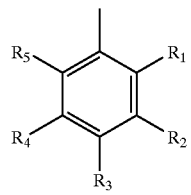

wherein $R_1$, $R_2$, $R_3$, $R_4$ and $R_5$ are each independently, hydrogen, a $C_1$–$C_4$ lower alkyl, a halogen, an amino group from the group consisting of NH$_2$, NHR and NRR' where R and R' are each a $C_1$–$C_4$ lower alkyl, a phenyl, or an alkoxy group.

3. The compound of claim 1 wherein said aryl is phenyl.

4. The compound of claim 1 wherein said methyl includes exactly one deuterium atom.

5. The compound of claim 1 wherein said methyl includes exactly two deuterium atoms.

6. The compound of claim 1 wherein said methyl includes exactly three deuterium atoms.

7. The compound of claim 3 wherein said methyl includes exactly one deuterium atom.

8. The compound of claim 3 wherein said methyl includes exactly two deuterium atoms.

9. The compound of claim 3 wherein said methyl includes exactly three deuterium atoms.

10. A process of preparing a [$^2$H$_1$, $^{13}$C], [$^2$H$_2$, $^{13}$C] and [$^2$H$_3$, $^{13}$C]methyl aryl sulfide comprising:

reacting a methanol from the group consisting of [$^2$H$_1$, $^{13}$C], [$^2$H$_2$, $^{13}$C] and [$^2$H$_3$, $^{13}$C]methanol with hydriodic acid to form a product mixture including volatile [$^2$H$_1$, $^{13}$C], [$^2$H$_2$, $^{13}$C] and [$^2$H$_3$, $^{13}$C]methyl iodide;

passing said volatile [$^2$H$_1$, $^{13}$C], [$^2$H$_2$, $^{13}$C] and [$^2$H$_3$, $^{13}$C]methyl iodide directly into a biphasic mixture including aqueous sodium hydroxide, benzene, and an arylthiol; and, maintaining said biphasic mixture for time sufficient to form [$^2$H$_1$, $^{13}$C], [$^2$H$_2$, $^{13}$C] and [$^2$H$_3$, $^{13}$C]methyl aryl sulfides.

11. The process of claim 10 wherein said aryl is selected from the group consisting of 1-naphthyl, substituted 1-naphthyl, 2-naphthyl, substituted 2-naphthyl, and phenyl groups with the structure

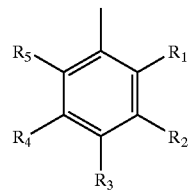

wherein $R_1$, $R_2$, $R_3$, $R_4$ and $R_5$ are each independently, hydrogen, a $C_1$–$C_4$ lower alkyl, a halogen, an amino group from the group consisting of NH$_2$, NHR and NRR' where R and R' are each a $C_1$–$C_4$ lower alkyl, a phenyl, or an alkoxy group.

12. A labeled compound, [$^2$H$_1$, $^{13}$C]methyl iodide.

13. A labeled compound, [$^2$H$_2$, $^{13}$C]methyl iodide.

14. A process of preparing a deuterated $^{13}$C methyl iodide selected from the group of [$^2$H$_1$, $^{13}$C]methyl iodide and [$^2$H$_2$, $^{13}$C]methyl iodide comprising:

reacting a compound selected from the group consisting of [$^2$H$_1$, $^{13}$C]methyl phenyl sulfide and [$^2$H$_2$, $^{13}$C]methyl phenyl sulfide with benzyl iodide for time sufficient to form [$^2$H$_1$, $^{13}$C]methyl iodide and [$^2$H$_2$, $^{13}$C]methyl iodide.

* * * * *